United States Patent [19]
Deucher et al.

[11] Patent Number: 5,097,497
[45] Date of Patent: Mar. 17, 1992

[54] DEPLOYABLE CT MEDICAL SYSTEM

[75] Inventors: Joseph S. Deucher, Lyndhurst; Anton Z. Zupancic, Kirtland; Charles A. Gardner, Ashtabula; Frank J. Oblak, Euclid; Anthony A. Champa, Cleveland, all of Ohio

[73] Assignee: Picker International, Inc., Highland Hts., Ohio

[21] Appl. No.: 663,575

[22] Filed: Mar. 1, 1991

[51] Int. Cl.$^5$ .............................. H05G 1/00; A61B 6/03
[52] U.S. Cl. .......................................... 378/204; 378/4; 378/196; 378/198
[58] Field of Search ....................... 378/4, 19, 20, 117, 378/118, 193, 195–198, 203, 204, 208–209

[56] References Cited
U.S. PATENT DOCUMENTS

| | | | |
|---|---|---|---|
| 4,935,949 | 6/1990 | Fujita et al. | 378/4 |
| 4,977,588 | 12/1990 | Van der Ende | 378/4 |
| 5,014,293 | 5/1991 | Boyd et al. | 378/4 |

FOREIGN PATENT DOCUMENTS 1213565  3/1966  Fed. Rep. of Germany ...... 378/198

OTHER PUBLICATIONS

Aeroflex Isolators Selection Guide Brochure.
Army Family ISO Shelters.

*Primary Examiner*—Janice A. Howell
*Assistant Examiner*—David P. Porta
*Attorney, Agent, or Firm*—Fay, Sharpe, Beall, Fagan, Minnich & McKee

[57] ABSTRACT

In a stowed configuration, a gantry (32) of a CT scanner is mounted by helical, wire rope shock isolators (78) to a floor (12) of an ISO shelter at about a 60° angle relative to a central axis (48) of the shelter. Mechanical assemblies (84, 100) limit movement of a tiltable gantry portion (82) relative to fixed gantry portions (60, 62, 64). A CT scanner control console (36) is mounted adjacent an opposite end of the ISO shelter on shock isolators (140). A patient couch (34) is mounted on shock isolators (122) in a stowed configuration in the available space between the gantry and the console. To deploy the system, foldable walls (26, 30), a foldable ceiling panel (28), and a foldable floor panel (24) of the ISO shelter are folded out. The patient couch is lowered onto casters (124) and moved into alignment with a central axis of the gantry. Jacks (128, 130) lower the patient couch from the casters and shock isolators onto the floor of the ISO shelter for fixed engagement. Jacks (70) lower the gantry from the isolators (78). Pivotal panels (42) of a lead screened viewing windows are pivoted about hinges (150) and lock (152) into an operating position. A track (162) is positioned over a patient access (54) to the ISO shelter and a lapped lead fabric curtain (190) is hung by hangers (170) from the track.

20 Claims, 11 Drawing Sheets

1

DEPLOYABLE CT MEDICAL SYSTEM

BACKGROUND OF THE INVENTION

The present invention relates to the mobile medical diagnostic art. It finds particular application in conjunction with a CT scanner mounted in a standard military ISO shelter for rapid deployment and will be described with particular reference thereto. However, it is to be appreciated that the invention will find application in conjunction with other types of medical diagnostic equipment in combination with other types of combined housing and transportation structures.

The U.S. military has set specifications for a standard military tactical shelter, also known as an ISO shelter, for various personnel uses. The ISO shelter is roughly 8'×8'×16' and is designed to be readily moved using standardized handling techniques. The shelters are utilized analogous to a trailer or small portable building for office facilities, medical facilities, and the like.

The Army specifications also provide for expandable ISO shelters. Specifically, an ISO 2:1 shelter expands to about twice the size of a single ISO shelter. One long wall has several hinged wall layers such that upon deployment, the side wall folds down to become about an 8'×20' floor, another section folds up to become the front wall, a third section folds out to function as the roof, and two side panels fold out to complete the double ISO shelter. The Army specifications analogously set forth ISO 3:1 shelters in which both side walls fold out to expand the shelter to triple size.

Various medical treatment facilities and diagnostic equipment have been housed in military ISO shelters. In addition to physicians' offices, the ISO shelters have been used to house conventional x-ray equipment. Although conventional radiography and fluoroscopy are available in the medical facilities for deployed military forces, there are physiological conditions that are best examined by CT scanners. Neurosurgical and ophthalmological specialties, for example, are not well-suited to conventional x-ray. The diagnosis and management of abdominal, thoracic, and spinal conditions with conventional x-ray equipment are limited. Although metal elements show up well with conventional x-ray, plastics and other synthetic materials found in the modern battlefield can be detected only poorly, if at all with conventional x-ray.

Although the above-referenced conditions can better be handled with CT scanners, CT scanners are delicate, complex, and large pieces of equipment. Their very precise alignments, large masses, and delicate moving parts are not conducive to movement. A CT scanner installation in a hospital can take days to set up, assemble, calibrate, and put into service. Deployable medical systems, particularly for military use, must be rendered functional rapidly upon being unloaded from the transportation vehicles.

The present invention enables a CT or other diagnostic scanner to be mounted in a standard ISO shelter for rapid military deployment.

SUMMARY OF THE INVENTION

In accordance with the present invention, a CT scanner is mounted in an ISO structure.

In accordance with a more limited aspect of the present invention, the ISO structure is an expandable ISO structure and the gantry is mounted in the ISO structure such that its central axis is at about a 60° angle to the longitudinal axis of the ISO structure. The patient support couch is stowed in one position for transport and is moved to an operational position in alignment with the central axis of the gantry when deployed. The angle of the gantry relative to the ISO structure varies with the size and construction of the gantry. The angle is selected such that the gantry fits completely within a single ISO structure unit both during shipment and operation. The angle is also selected such that when the couch is connected with the gantry along the central axis, the couch is readily accessible from either side such that a patient can be loaded from either side of the couch without interference from the walls of the ISO structure.

In accordance with a more limited aspect of the present invention, the gantry and couch are mounted on vibration and shock absorbing structures in their stowed configurations and are rigidly mounted to the ISO structure in their operational configuration. The patient couch also has means, such as wheels, to facilitate movement of the couch from its stowed position to its operational position.

In accordance with another aspect of the present invention, an electrical interlock is provided which prevents the gantry from being operated when the gantry is stowed for shock and vibration isolation rather than being rigidly mounted to the ISO structure.

In accordance with another aspect of the present invention, snubbers are provided for controlling sway of the gantry during transportation.

In accordance with another aspect of the present invention, structure is added to rigidize the gantry when it is supported by the shock and vibration isolation mechanisms.

In accordance with another aspect of the present invention, a control console is also mounted in the ISO structure. Pivoted, leaded screen viewing panel assemblies are mounted adjacent the console to protect the operator from incident radiation. The lead screen panel assemblies are movable to accommodate additional observers or operators.

In accordance with another aspect of the present invention, the operator console is selectively supported on shock and vibration isolation means.

In accordance with another aspect of the present invention, a multi-panel leaded curtain is hung across an access opening to allow door-free access while preventing the leakage of incident radiation.

In accordance with another more limited aspect of the present invention, the leaded curtain is mounted on a slide bar, which slide bar is stowed with one portion of the ISO shelter by a quick connect mounting means and is mounted across the access opening with the quick connect means in an operational configuration.

In accordance with another more limited aspect of the present invention, accessories are mounted to walls of the ISO structure. The accessories include a light box, couch accessories, and the like.

One advantage of the present invention is that it enables a CT scanner to be deployed rapidly in remote locations.

Another advantage of the present invention is that it provides ready access to the patient couch. The couch is accessible from either side with stretchers or gurneys on which an unconscious patient may be transported.

Another advantage of the present invention is that the operator and observers can readily view the patient during the examination.

Another advantage of the present invention is that the gantry of the CT scanner is freely movable over the full range of normal operation.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
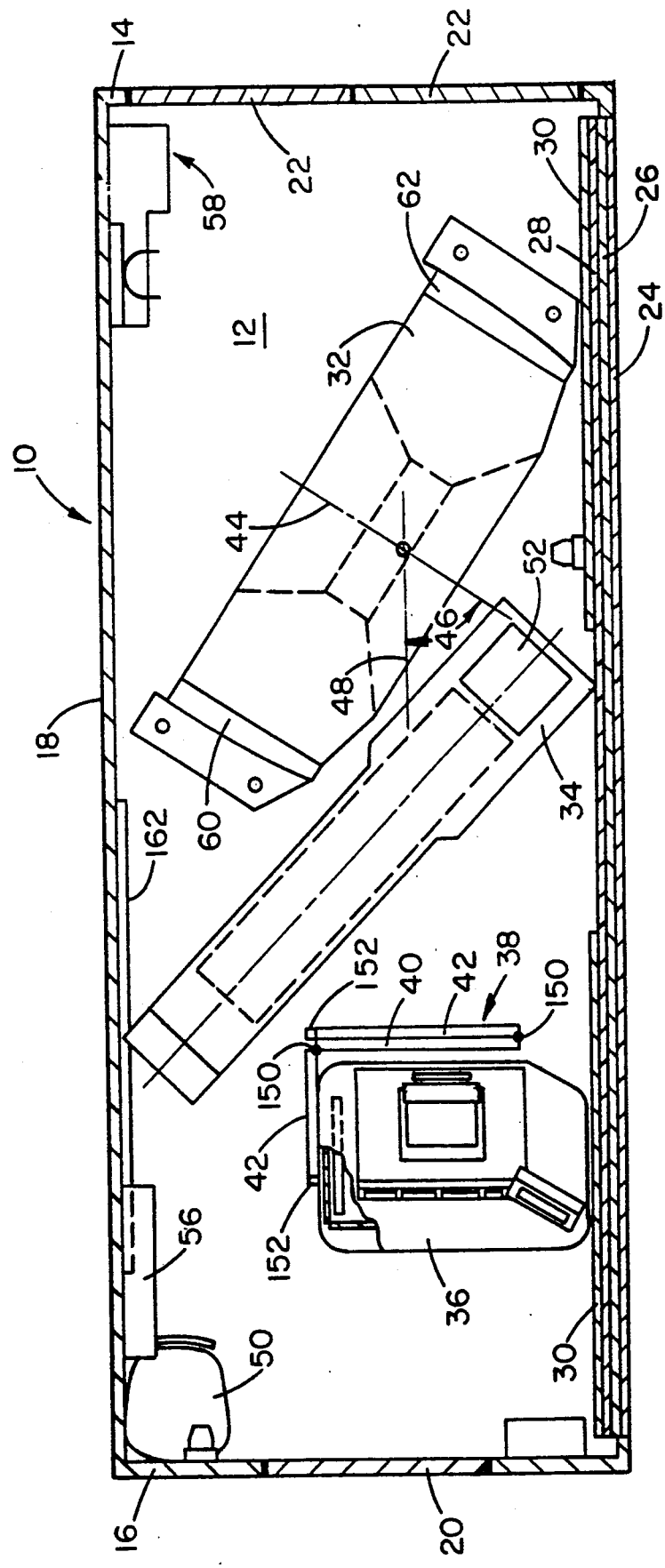
FIG. 1 is a top plan view of a combination CT scanner and ISO shelter in the stowed configuration in accordance with the present invention.
Figure 1A:
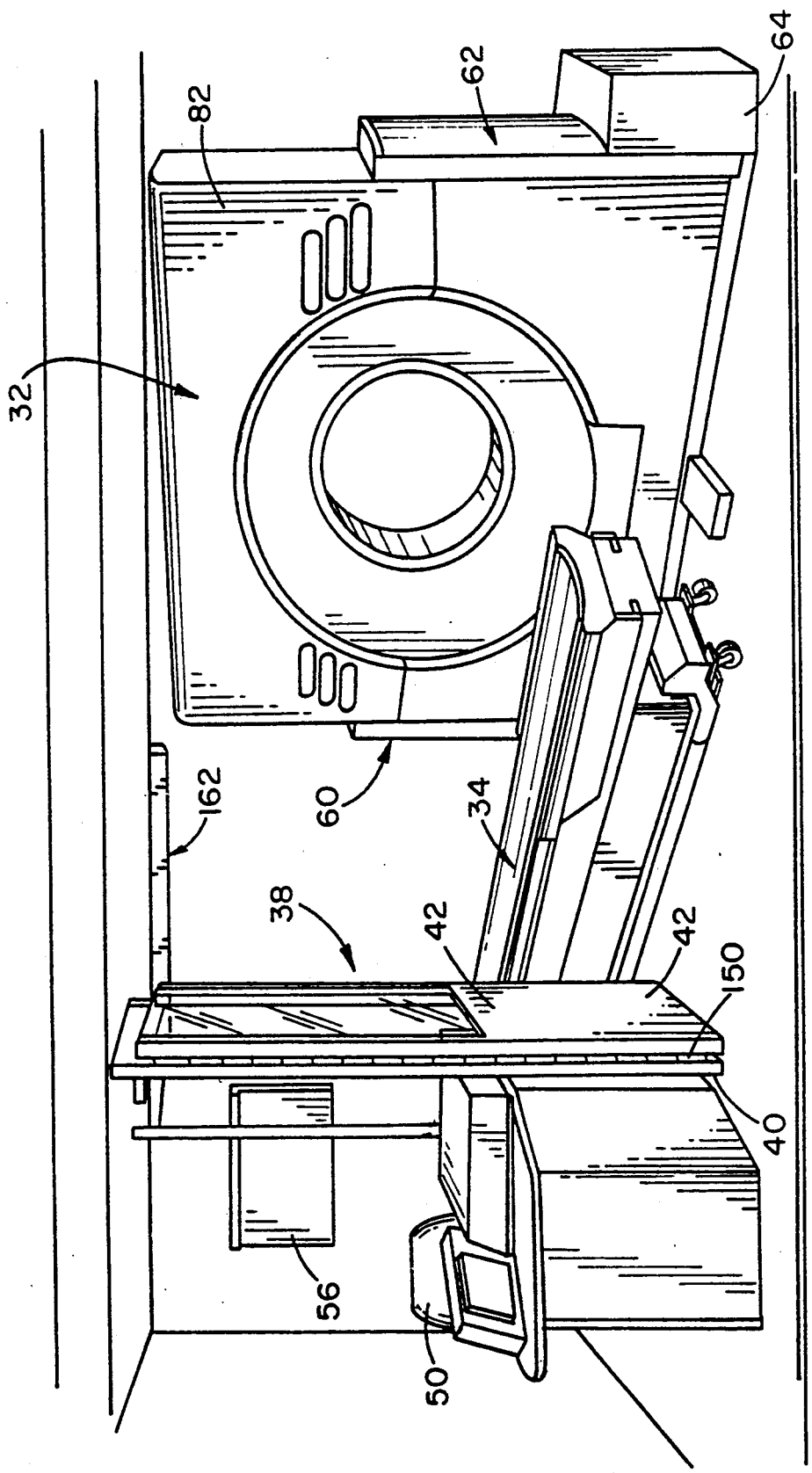
FIG. 1A is a front perspective view of the combination of FIG. 1 from the patient access door with the shelter expanded.
Figure 2:
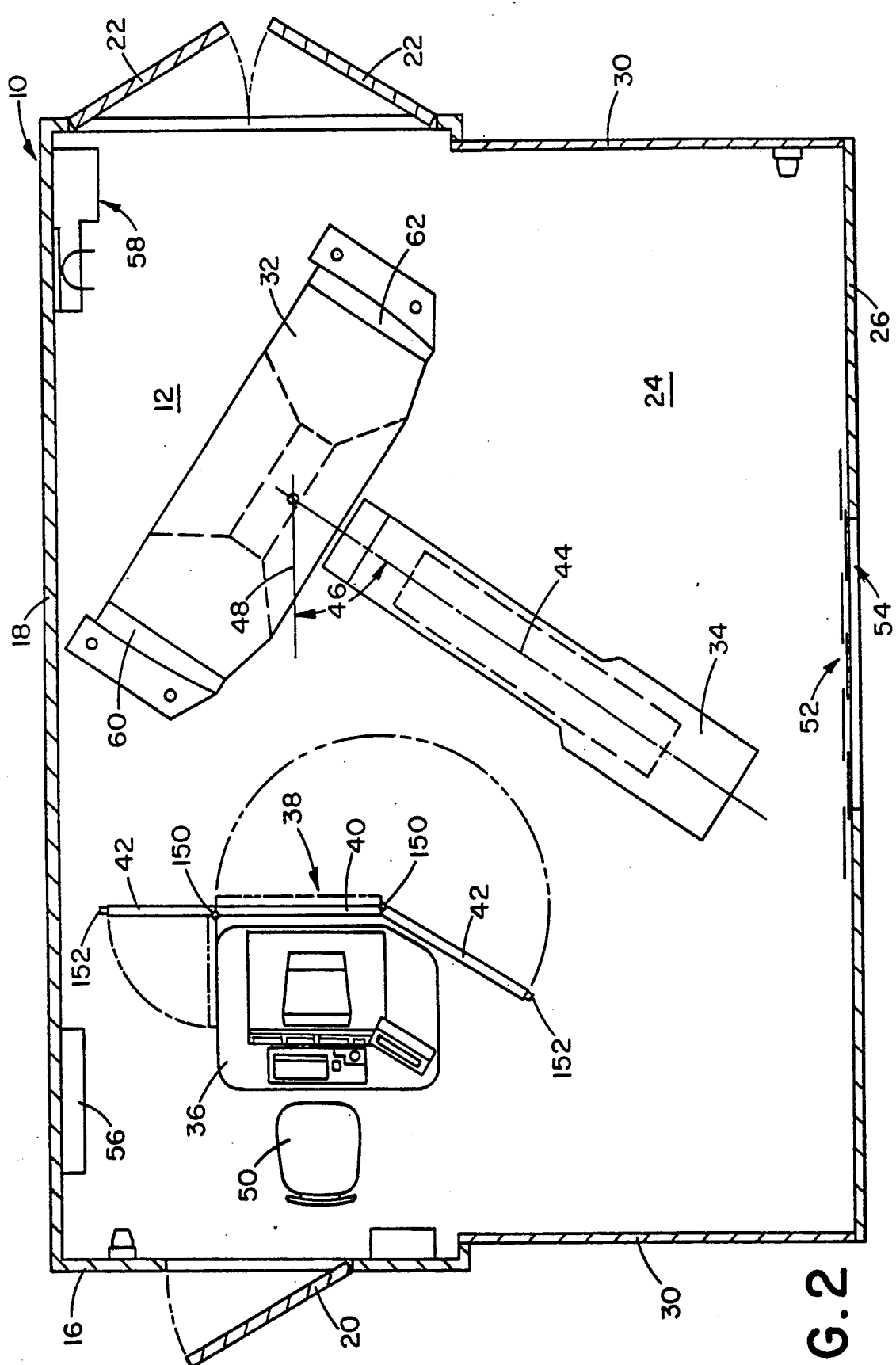
FIG. 2 is a top plan view in partial section of the combination of FIG. 1 in the operational configuration.
Figure 2A:
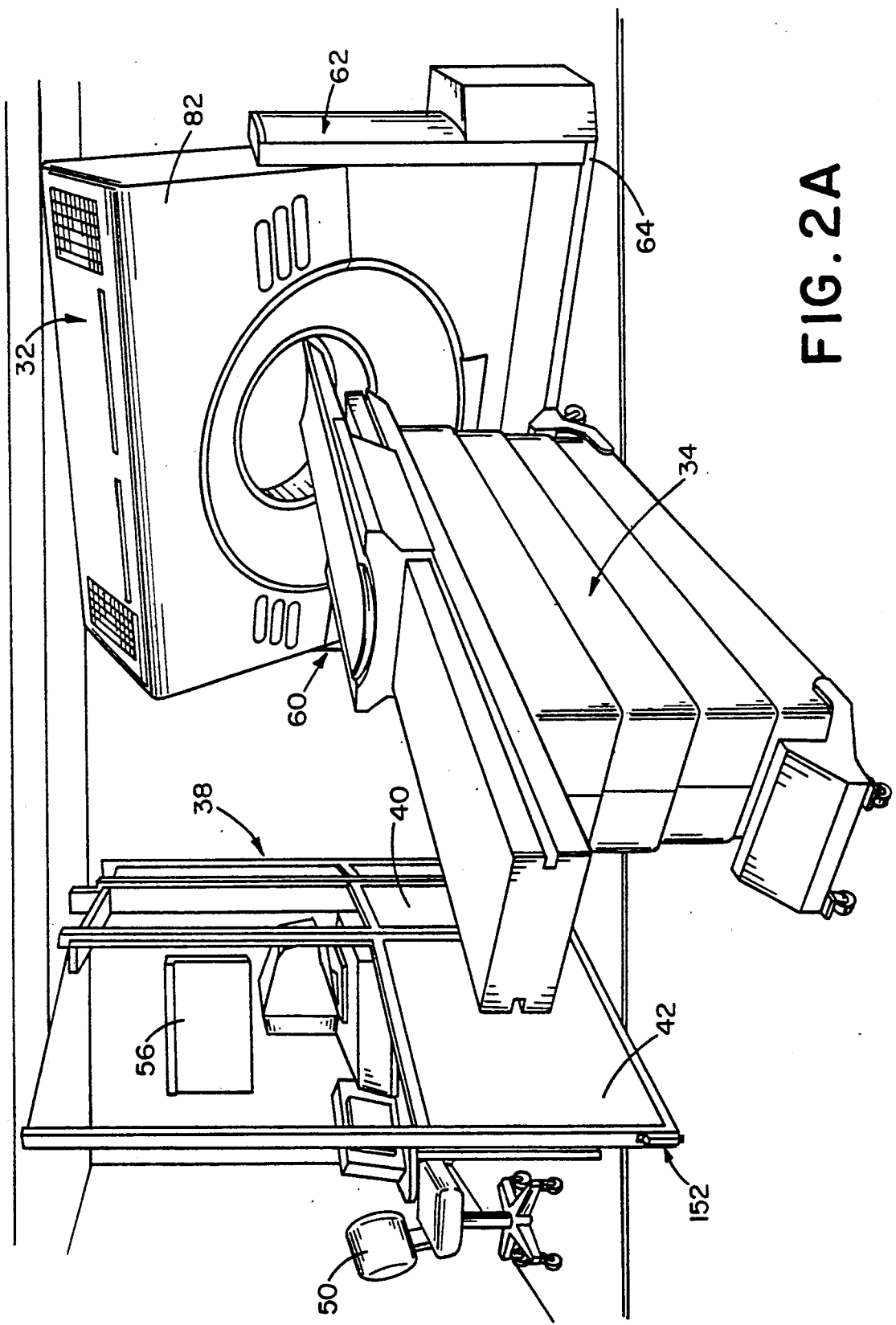
FIG. 2A is a front view of the combination of FIG. 2 from the patient access door.

With reference to FIGS. 1 and 2, an ISO shelter 10 has a fixed floor 12, fixed end walls 14, 16, and an elongated side wall 18. An operator access door 20 is defined in one of the walls and equipment access doors 22 are defined in another. One long, side wall of the ISO shelter is defined by a floor portion 24, vertical wall 26, roof 28, and pair of hinged end walls 30. The floor portion 24, vertical wall 26, roof 28, and end walls 30 fold out to double the size of the shelter (FIG. 2).

A CT scanner assembly is disposed inside the ISO shelter. The CT scanner assembly includes a gantry 32, a patient couch 34, and an operator's console 36. A hinged, lead screened viewing window assembly 38 includes a fixed panel 40 to which side panels 42 are hingedly mounted. The gantry 32 is mounted such that its central axis 44 is mounted about an angle 46 of 30°–90°, preferably 60°, relative to a longitudinal axis 48 of the ISO shelter.

When the ISO shelter is delivered to the location at which it is to be set up, the ISO shelter is expanded, as is conventional. The patient couch 34 is moved from a stowed position (FIG. 1) to an operational position (FIG. 2) with its longitudinal axis centered on the gantry central axis 44. An operator chair 50 is moved from its stowed position to a position adjacent the operator's console. A lead curtain 52 is hung across an access doorway 54 in the vertical wall 26. A physician's light box 56 is disposed to be shielded by the hinged lead screened viewing glass 42. Couch accessories 58 such as head and neck supports, cushions, and the like are removably mounted to a shelter wall.

In the stowed configuration of FIG. 1, the gantry, patient couch, and operator console are all suspended on shock isolating means or assemblies. These assemblies are defeated in the operational configuration (FIG. 2) such that at least the gantry and patient couch are mounted firmly to the ISO shelter floor.

Figure 3:
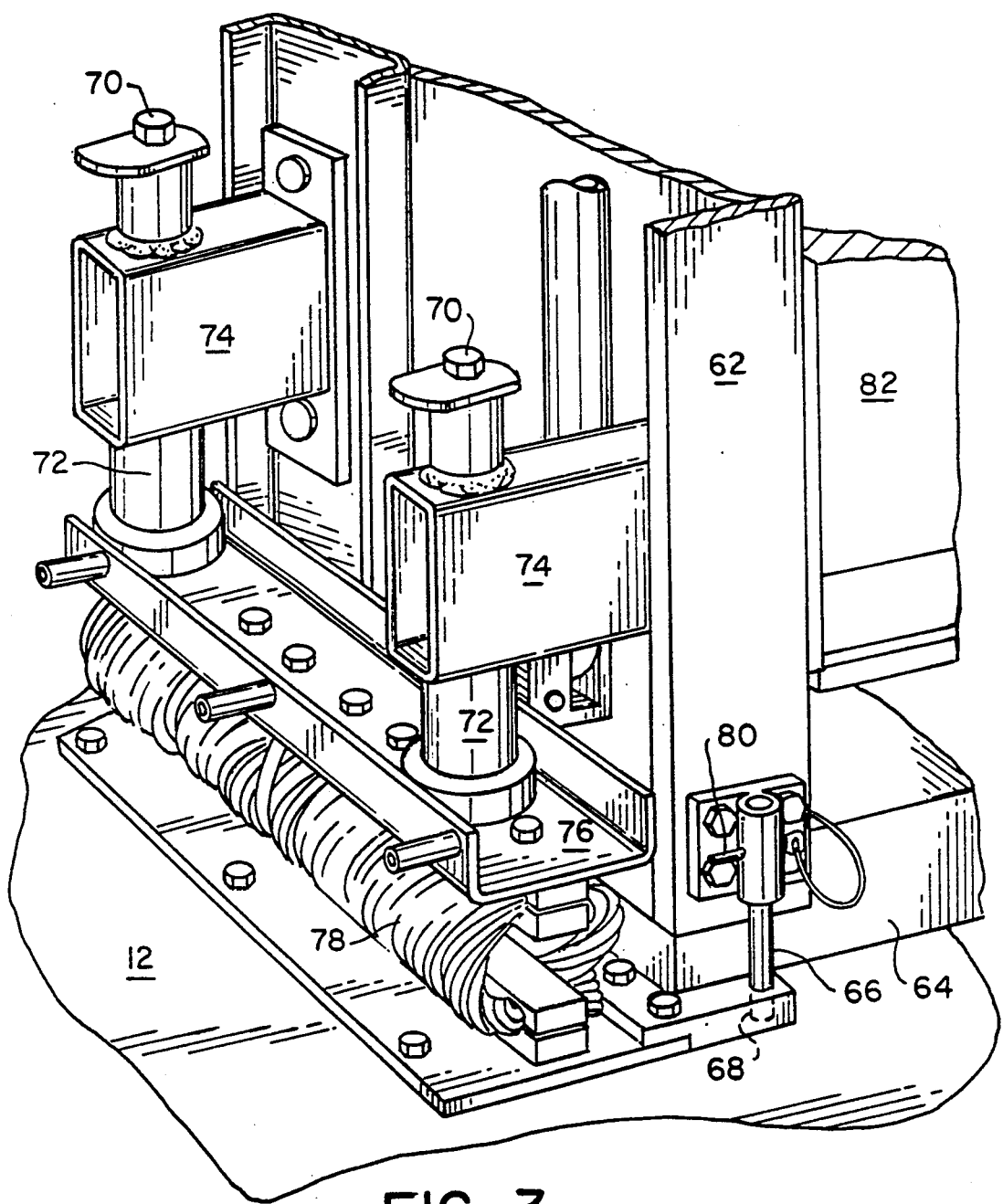
FIG. 3 is a perspective view of the gantry shock isolation mounting assembly.

With reference to FIG. 3 and continuing reference to FIGS. and 2, the gantry 32 includes side frame portions 60, 62 which extend upward from a base 64. In the operational configuration, the base rests securely on the floor 12 of the ISO shelter and its position is fixed by alignment pins 66 which are selectively received in apertures 68 mounted to the ISO shelter floor. To stow the gantry, jack screws 70 located at the four corners of the gantry are rotated relative to threaded bushings 72 in side frame extensions 74. This rotation causes displacement of bushing 72 relative to a plate 76 that is supported on a coiled, metal rope isolator 78. As the jack screw is rotated, the gantry is lifted and supported on isolator 78 and a like isolator on the other side. The alignment pin 66 is retracted and locked in the retracted stowed position by a locking pin 80. In this manner, the gantry is isolated from shocks which the ISO shelter may suffer when being moved.

To deploy the scanner, the alignment pins 66 are extended. The jack screws are contracted lowering the base 64 onto the floor. The interaction of the alignment pins and bushings 68 assure that the gantry is precisely positioned on the floor in a presented location.

Figure 4:
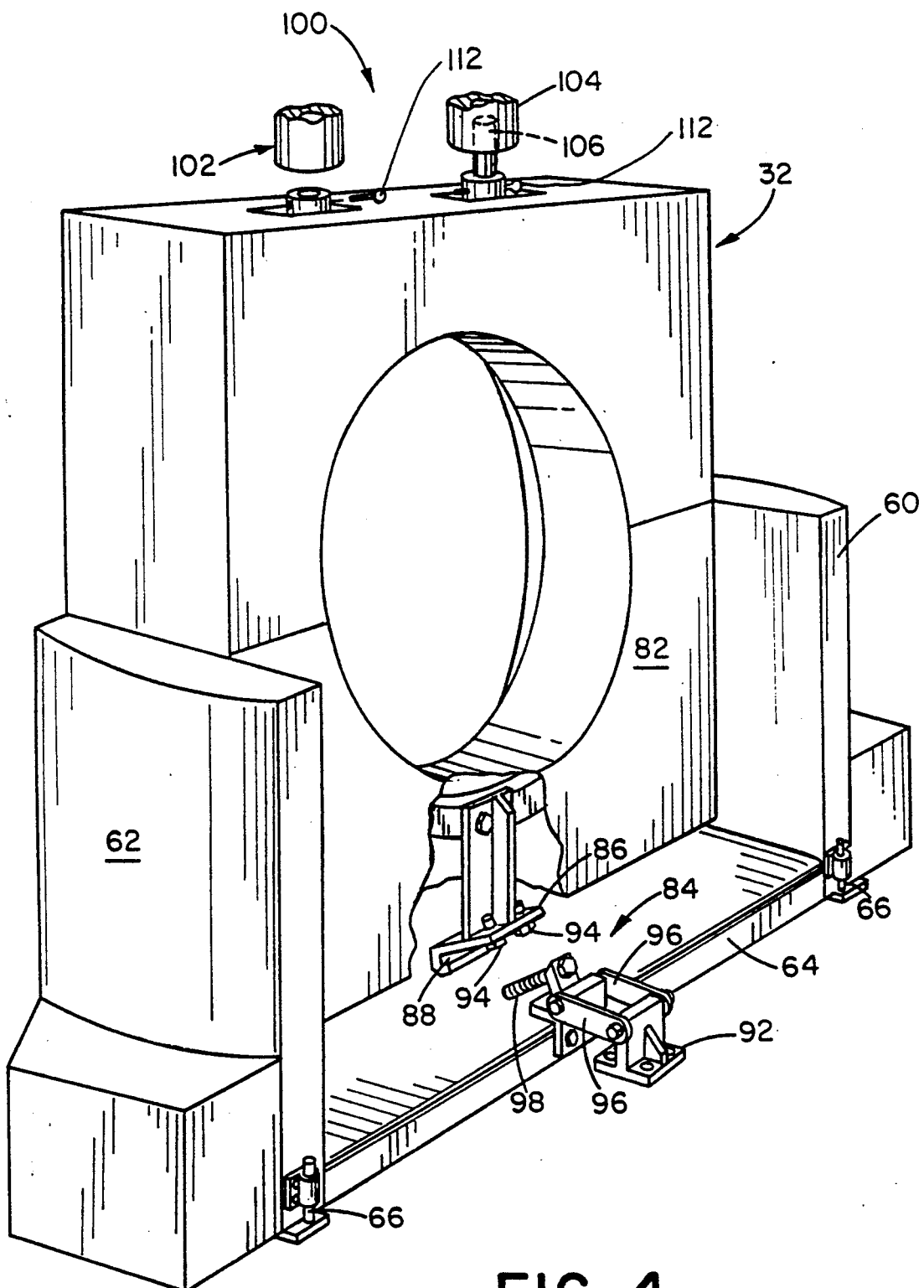
FIG. 4 is a rear, perspective view of the gantry illustrating mechanical devices for preventing a tilting portion of the gantry from moving.
Figure 5:
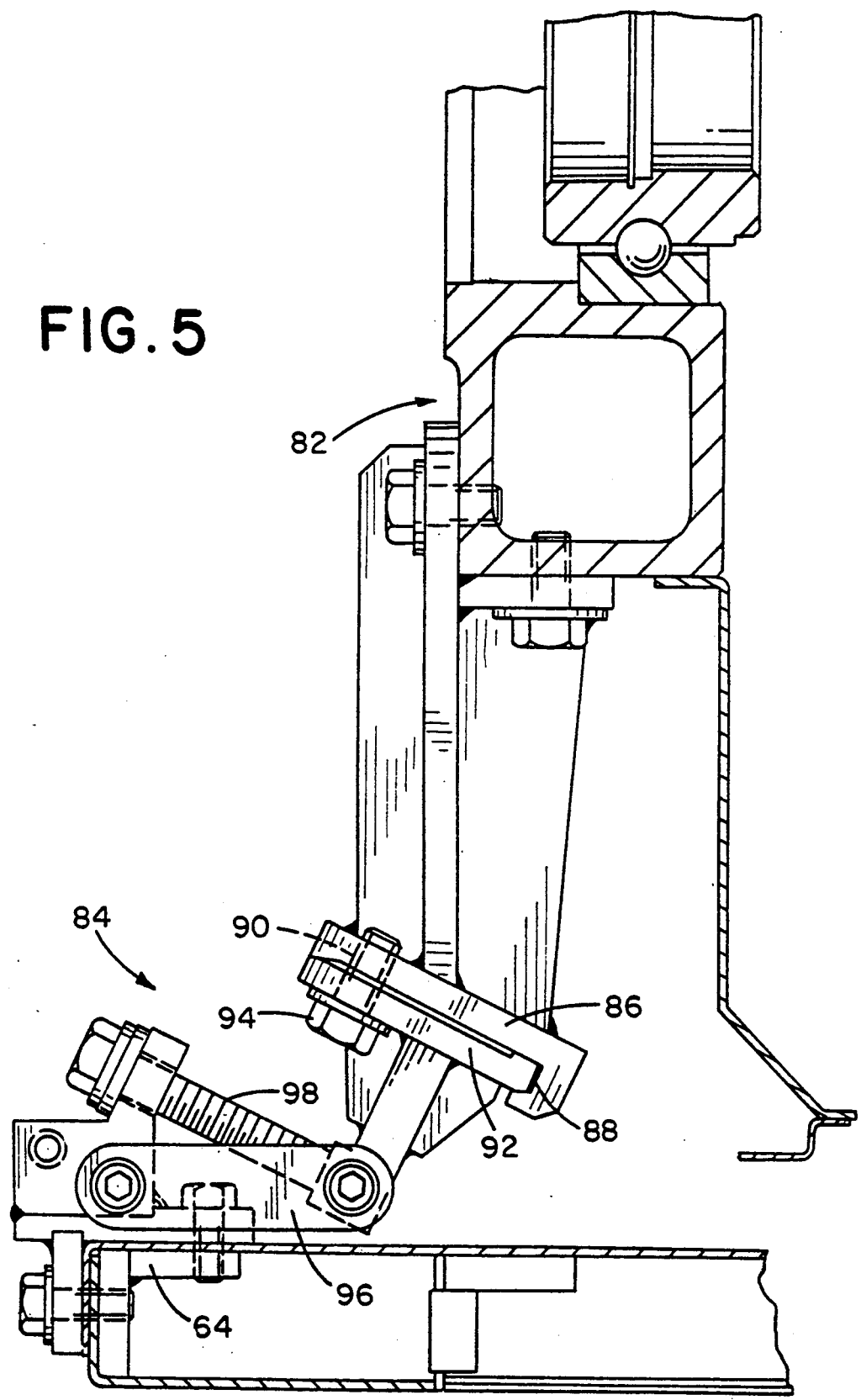
FIG. 5 is a side view of the tilt locking device of FIG. 4.

The gantry 30 includes a tiltable gantry portion 82 that is mounted for rotation about a horizontal axis between the gantry frame portion 60, 62. As illustrated in FIGS. 4 and 5, a bracket assembly 84 is provided to lock the movable gantry portion 82 relative to the stationary portion 64. More specifically, a stationary bracket 86 extending from the movable gantry portion 82 defines a slot 88 and a pair of threaded apertures 90. A movable bracket 92 is selectively received in the slot 88 and fixed by bolts 94 extending through apertures in the movable bracket 92 into the threaded apertures 90. The movable bracket 92 is connected by links 96 to a bracket mounted to the gantry base 64. A draw bolt 98 selectively engages the back side of the movable bracket 92 to fix the links 96 against flexing in the stowed configuration.

In the operational configuration, the draw bolt 98 is loosened and the bolts 94 removed enabling the links 96 to shift the movable bracket 92 around and against the floor 12 of the ISO shelter allowing the movable portion 82 of the gantry to be tilted.

Figure 6:
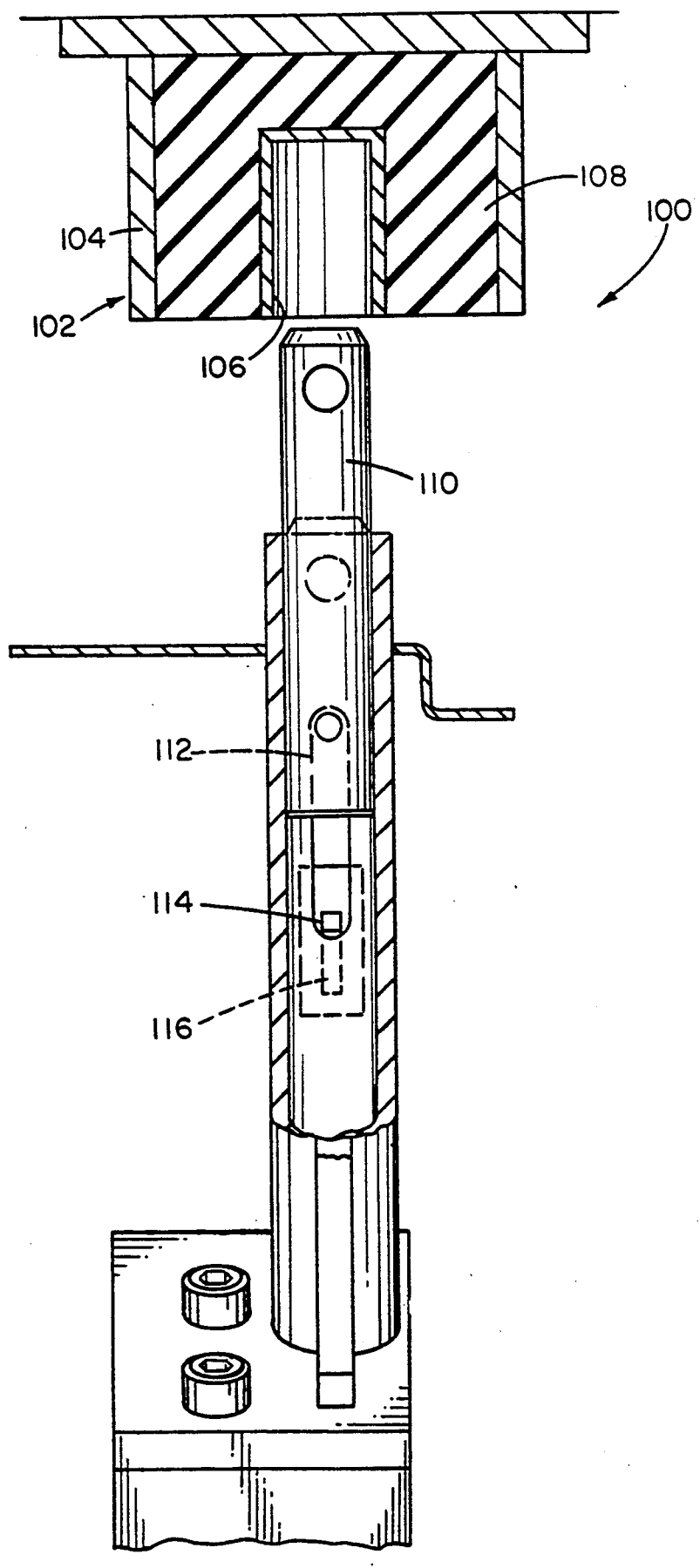
FIG. 6 is a side view in partial section of the gantry side-to-side motion limiting assembly of FIG. 4.

With reference to FIGS. 4 and 6, not only is it undesirable for the movable portion of the gantry to tilt, it is also undesirable for the gantry to move side-to-side or lift from the floor so high that engages the ceiling. To this end, an alignment and tilting preventing means 100 including a pair of snubber means 102 is provided. A metal outer wall 104 and a sleeve 106 defining a central bore are separated from each other by an elastomeric material 108. Retractable pins 110 selectively extend from an upper surface of the movable gantry portion into the snubber bores 106. Removable keys 112 lock the alignment pins extended or retracted. Interaction between the pins and the bores prevent the gantry from tilting or moving side-to-side. The elastomeric material 108 absorbs shocks and inhibits the gantry from being propelled against the ceiling of the ISO shelter. Each of the pins has a surface 114 that interacts with an interlock switch 116. The interlock switch is connected between the gantry control panel and a motor (not shown) for tilting the gantry portion 82 relative to stationary gantry portions 60, 62, 64. The interlock switches 116 prevent the operator from attempting to tip the gantry when the alignment pins 110 are extended.

Figure 7:
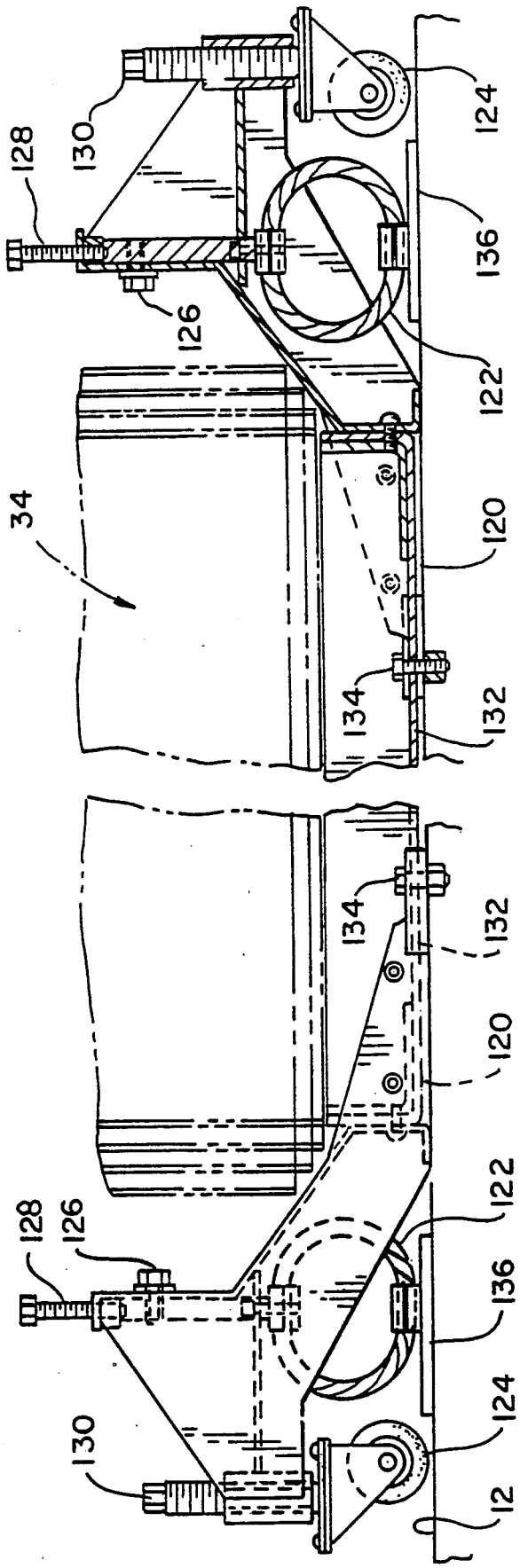
FIG. 7 is a side view illustrating shock isolation and caster mounting arrangements of the patient couch.

With reference to FIG. 7, the patient couch 34 rests on a base portion 120 in the operational configuration, and is supported by wheels 124 when being moved between the stowed and operational positions. In the stowed position, a locking bolt 126 is released enabling a first jack screw 128 to be turned down to lift the patient couch off the shelter floor 12 such that it is supported on the helical, wire rope isolators 122.

To move the patient couch from the stowed to the operational positions, a second jack screw 130 is rotated to extend wheels or casters into contact with the floor. The first jack screw 128 is then turned in the opposite direction to retract the helical, wire rope isolators leaving the patient couch supported on the wheels or rollers. The patient couch is then wheeled to the operational position, i.e. in alignment with the central axis 44 of the CT scanner. This central axis may vary between 30° and 90° from the ISO shelter longitudinal axis 48, depending on the exact geometry of the scanner and couch selected. The angle is selected such that there is ready access to both sides of the patient couch with a patient on a gurney, without blocking access through the patient access door. In the illustrated embodiment, an angle of about 60° is optimum. Once the patient couch is aligned with the gantry, the wheels or casters are retracted by rotating the second jack screw 130 in the opposite direction until the base 120 of the patient couch rests on the floor. The patient couch has flanges 132 which receive bolts 134. These flanges are aligned with pre-tapped threaded sockets in the floor 12 of the ISO shelter to assure that the couch is accurately positioned along the central axis of the gantry.

To return the patient couch to the stowed position, the procedure is reversed. The second jack screw 130 lowers the wheels 124. The couch is rolled to the stowed position, where the wire spring assemblies are extended as the wheels are retracted. Base plates 136 on the helical, wire rope isolators have apertures which align with the pre-tapped bores in the floor of the ISO shelter. Bolts pass through the apertures into the tapped bores to fasten the couch to the floor in the stowed position.

Figure 8:
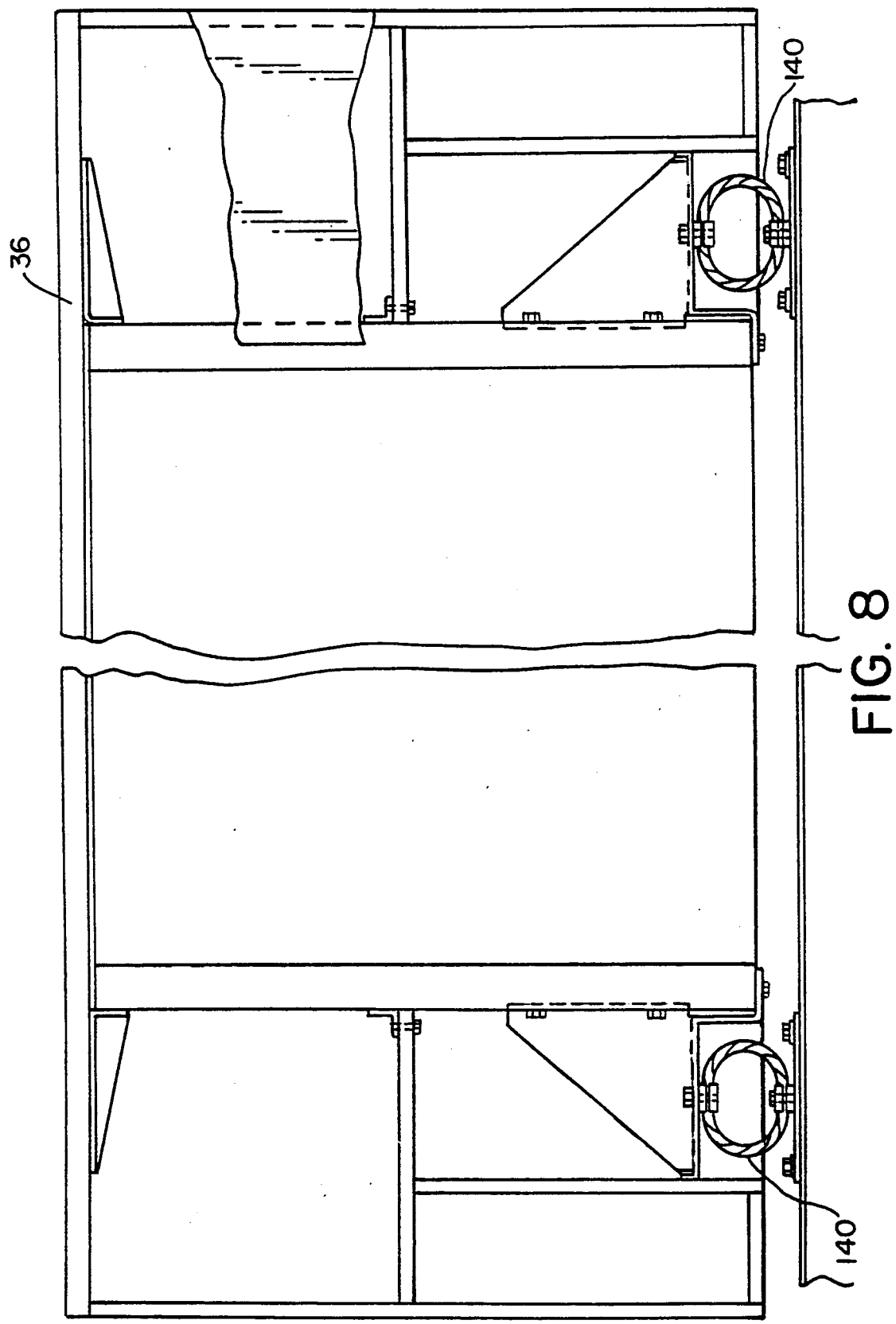
FIG. 8 is a front view of the console of FIG. 1 illustrating the shock isolation assemblies; and, FIG. 9 illustrates details of the leaded curtain assembly of FIG. 2.

With reference to FIG. 8, the console 36 is mounted on a pair of helical, wire spring isolators 140. Although mechanisms may be provided analogous to those discussed in conjunction with the gantry and the patient support table for mounting the console directly to the floor, the console functions satisfactorily when supported by the isolators. Accordingly, in the preferred embodiment, the console is supported by the isolators in both the stowed and operational configurations.

With reference again to FIGS. 1 and 2, the lead screened viewing windows stationary panel 40 is fixed to the front of the patient console. Hinges 150 connect the two side panels 42. A locking means 152 is provided for selectively fixing the position of each of the movable side panels. The locking means may include a slide pin that is selectively received in an aperture in the floor. Such a slide pin is particularly advantageous for holding the panels in the stowed configuration. Additional apertures may be provided in the floor for locking the screens in other positions during operation. Alternately, structures which permit positioning of the lead screened viewing windows in plurality of positions may be provided, such as providing a spring bias and rubber contact tip on the alignment pin, friction hinges, catches or detents on the hinges, or the like.

Figure 9:
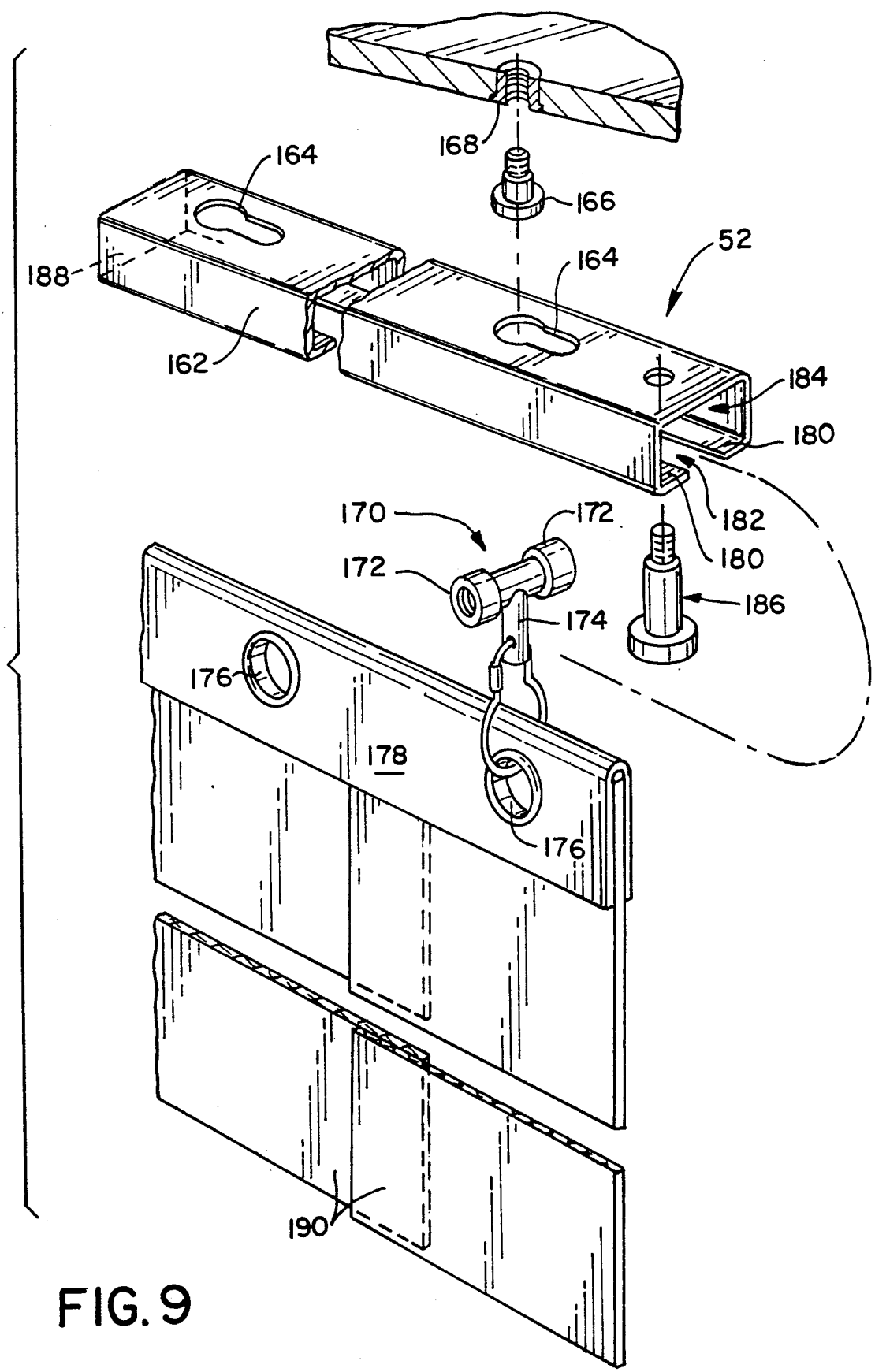

With reference to FIG. 9, the lead curtain assembly 52 includes a track 162 with a quick connect mounting means for mounting the track quickly to the ceiling of the extended portion of the ISO shelter across the patient access opening. The quick mounting means of the preferred embodiments includes keyhole mounting slots 164 along one surface of the rod which are received on shouldered mounting screws 166 previously mounted in a threaded bushing 168 in the ceiling. A curtain hanger 170 has rollers 172 at either end and a downward depending portion 174 for selective interengagement with grommets 176 along an upper hem 178 of the lead curtain assembly 52. The track 162 has lower track portions 180 and a central slot 182 through which the downward depending portion 174 extends. Interaction between the rollers 172 and the track portions 180 enable the curtain to be readily positioned along the rail. Once all the curtain hangers are slid into an open end 184 of the rail, a stop means 186 is extended through the slot and an aperture in the rail to engage a pre-tapped threaded bore in the ceiling. The track is closed at a second end 188 to retain the hangers in the track. The stop not only locks the curtain hangers from exiting the open end of the track but also prevents the track from being shifted sufficiently that the enlarged portion of the keyhole apertures 164 can become aligned with the head of the ceiling mounting screws 166. A plurality of overlapping leaded fabric strips 190 are sewn into the hem 178 and hang downward from the hem and grommets.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A deployable CT medical system comprising:
   an expandable, portable shelter, the shelter including a fixed floor portion, opposite shorter wall portions and a longer wall portion extending therebetween along a first side of the shelter;
   a plurality of foldably interconnected wall, ceiling, and floor portions extending along a second side of the shelter, the folded portions being selectively unfoldable to expand the shelter;
   a CT scanner gantry mounted to the fixed floor portion of the shelter;
   a console for controlling the CT scanner gantry, the console being mounted to the fixed floor portion;
   a patient couch mountable in the shelter.

2. The system as set forth in claim 1 wherein the gantry is mounted such that a central axis thereof is at an angle in the range of 30°-90° relative to a longitudinal axis of the shelter and wherein the patient couch is mountable in at least two positions, one of which is in alignment with the gantry central axis.

3. The system as set forth in claim 2 wherein the angle is substantially 60°.

4. The system as set forth in claim 1 further including isolation means for isolating the gantry, the patient couch, and the console from shock and vibration incurred when the shelter is moved.

5. The system as set forth in claim 4 wherein the isolation means includes helical, wire rope isolators supporting the gantry, patient couch, and console.

6. The system as set forth in claim 4 further including a first couch jack means extending between the patient couch and the isolation means such that in a retracted position of the first couch jack means, the patient couch rests on the shelter floor and in an extended position, the patient couch is lifted from the shelter floor and supported by the first couch jack means on the isolation means.

7. The system as set forth in claim 6 further including a second couch jack means for selectively raising and lowering casters between raised positions and lowered positions in which the casters engage the shelter floor such that the patient couch is selectively movable on the casters along the shelter floor.

8. The system as set forth in claim 4 further including gantry supporting means for selectively supporting the gantry on (1) the isolation means and (2) the shelter floor.

9. The system as set forth in claim 8 wherein the gantry supporting means includes a jack means connected between the gantry and the isolation means such that when the jack means is in a retracted position, the gantry rests directly on the shelter floor and when the jack means is in extended configuration, the gantry is lifted from the floor and supported by the isolation means.

10. The system as set forth in claim 9 further including a retractable alignment pin mounted to the gantry and an alignment bushing mounted to the shelter floor for assuring that the gantry is accurately positioned in a preselected location as the jack means is retracted, lowering the gantry to the shelter floor.

11. The system as set forth in claim 8 further including at least one elastomeric member mounted to a shelter ceiling above the gantry, the elastomeric member defining a vertical bore partially therein, and wherein the gantry includes a retractable alignment pin which is selectively received in the bore such that interaction between the bore and the alignment pin limits side-to-side and tipping movement of the gantry.

12. The system as set forth in claim 11 wherein the gantry includes a tiltable gantry portion which is tiltable relative to a stationary gantry portion, the alignment pin being mounted on the tiltable gantry portion, and further including an interlock switch operatively connected with the alignment pin for preventing the operator from causing power to be supplied for selectively tilting the tiltable gantry portion when the alignment pin is engaged in the elastomeric member bore.

13. The system as set forth in claim 8 wherein the gantry includes a stationary portion and a tiltable portion and further including an auxiliary locking means for selectively mechanically locking the tilting portion of the gantry from tilting relative to the stationary gantry portion.

14. The system as set forth in claim 1 further including a stationary leaded screen viewing panel mounted between the console and the gantry and at least one movable leaded screen viewing panel hingedly mounted to one side of the stationary leaded screen viewing panel.

15. The system as set forth in claim 1 further including a film box mounted to one of the walls of the shelter.

16. The system as set forth in claim 1 wherein the shelter includes a patient access opening and further including a plurality of lapped leaded fabric strips hanging across the patient access opening and supported by a leaded strip mounting means.

17. The system as set forth in claim 16 wherein the leaded strip mounting means includes a track which is selectively connectable to the ceiling with quick connect coupling means and hangers which are movable along the track and which engage the leaded strips for hanging the leaded strips from the track.

18. A deployable medical diagnostic system comprising:
   an expandable, portable shelter, the shelter including a fixed floor portion, opposite fixed end wall portions, and a plurality of foldable, interconnected wall, ceiling, and floor portions which in a stowed configuration extend along a first side of the shelter between the fixed end wall portions and which in an operational configuration define floor, wall, and ceiling portions of an expanded portion of the shelter;
   a gantry mounted to the fixed floor portion of the shelter by isolating means for shock isolating the gantry from the fixed floor in the stowed configuration, a gantry jack means for selectively lowering the gantry from the isolation means to enable the gantry to be mounted to the fixed floor portion in the operational configuration;
   a console for controlling the gantry, the console being mounted on console isolation means for shock isolating the console from the fixed floor portion;
   a patient couch that is selectively mountable to the fixed floor portion in the stowed configuration and which is selectively mountable at least in part to the unfolded floor portion in the operational configuration, the couch including couch isolation means on which the couch is supported in the stowed configuration in shock isolation from the fixed floor, first couch jack means for selectively lowering the patient couch from the couch isolation means to enable the couch to be supported directly on the floor portions, and a second jack means for selectively extending caster means for enabling the couch to be movably supported on casters to facilitate movement of the couch between the stowed and operational configurations;
   a viewing panel assembly mounted between the console and gantry, the viewing panel assembly including at least two viewing panels which are movably interconnected to allow selective positioning of at least one of the viewing panels, and a locking means for locking the at least one movable viewing panel in each of a plurality of positions.

19. The system as set forth in claim 18 wherein the gantry includes a movable gantry portion which is movable relative to a stationary gantry portion and further including mechanical means for locking the movable gantry portion against movement relative to the stationary gantry portion.

20. The system as set forth in claim 19 further including a track mounted over a patient access opening to the shelter, a plurality of hangers movably received along the track, and a plurality of lapped, leaded fabric strips supported by the hangers.

* * * * *